US012402782B2

(12) United States Patent
Christensen et al.

(10) Patent No.: US 12,402,782 B2
(45) Date of Patent: Sep. 2, 2025

(54) ENDOSCOPE CONTROL SYSTEM (71) Applicant: AMBU A/S, Ballerup (DK)

(72) Inventors: Martin Johst Christensen, Copenhagen (DK); Günter Wilhelm Schütz, Augsburg (DE)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 17/239,373

(22) Filed: Apr. 23, 2021

(65) Prior Publication Data

US 2021/0338050 A1  Nov. 4, 2021

(30) Foreign Application Priority Data

Apr. 30, 2020 (EP) .................................... 20172237
Apr. 30, 2020 (EP) .................................... 20172238

(51) Int. Cl.
*A61B 1/00* (2006.01)
*A61B 1/005* (2006.01)
(Continued)

(52) U.S. Cl.
CPC .......... *A61B 1/0052* (2013.01); *A61B 1/0011* (2013.01); *A61B 1/0057* (2013.01); *B29C 65/58* (2013.01); *B29L 2031/753* (2013.01)

(58) Field of Classification Search
CPC ... A61B 1/0052; A61B 1/0011; A61B 1/0057; A61B 1/00105; A61B 1/00066;
(Continued)

(56) References Cited

U.S. PATENT DOCUMENTS 3,610,231 A    10/1971  Takahashi
4,012,155 A *  3/1977   Morris ............... A47B 87/0207
                                                           403/360
(Continued)

FOREIGN PATENT DOCUMENTS

EP    0306723 B1    3/1993
EP    0754429 B1    9/2004
(Continued)

OTHER PUBLICATIONS

EBay listing, steinelager.de, Wheel 32×64 Conical with Spikes and Inner 48 Tooth Gear 64712—Black, available at https://steinelager.de/en/category/7/wheel and https://www.steinelager.de/en/color/26/black, website copyright 2016-1029.
(Continued)

*Primary Examiner* — Anh Tuan T Nguyen
*Assistant Examiner* — Rynae E Boler
(74) *Attorney, Agent, or Firm* — Faegre Drinker Biddle & Reath LLP (57) ABSTRACT

An endoscope including a control system including: a first control wheel connected to a first wire drum and to a first steering wire of the endoscope to control the bending operation in a first dimension, the first control wheel having a bearing surface; a second control wheel connected to a second wire drum and to a second steering wire to control the bending operation in a second dimension, the second control wheel having an outer bearing surface positioned farther from the axis of rotation than the bearing surface of the first control wheel; and an outer bearing element including an inner bearing surface positioned farther from the axis of rotation than the outer bearing surface of the second control wheel and abutting the outer bearing surface of the second control wheel so that rotation of the second control wheel is at least partly borne on the outer bearing element.

20 Claims, 6 Drawing Sheets

(51) Int. Cl.
   *B29C 65/58* (2006.01)
   *B29L 31/00* (2006.01)
(58) Field of Classification Search
   CPC ....... G05G 1/12; F16B 21/082; F16B 21/086; F16B 21/084; F16B 21/088
   See application file for complete search history.

(56) References Cited

U.S. PATENT DOCUMENTS

| | | | |
|---|---|---|---|
| 4,207,873 | A | 6/1980 | Kruy |
| 4,461,282 | A | 7/1984 | Ouchi et al. |
| 4,473,301 | A | 9/1984 | Namyslo |
| 4,617,914 | A | 10/1986 | Ueda |
| 4,825,850 | A | 5/1989 | Opie et al. |
| 4,924,852 | A | 5/1990 | Suzuki et al. |
| 4,942,866 | A | 7/1990 | Usami |
| 5,014,685 | A | 5/1991 | Takahashi |
| 5,086,200 | A * | 2/1992 | Kline ............... H01H 19/115 200/11 R |
| 5,174,276 | A | 12/1992 | Crockard |
| 5,269,202 | A | 12/1993 | Kiyosawa et al. |
| 5,329,887 | A | 7/1994 | Ailinger et al. |
| 5,426,992 | A | 6/1995 | Morii et al. |
| 5,464,007 | A | 11/1995 | Krauter et al. |
| 5,507,717 | A | 4/1996 | Kura et al. |
| 5,512,035 | A | 4/1996 | Konstorum et al. |
| 5,575,755 | A | 11/1996 | Krauter et al. |
| 5,871,441 | A * | 2/1999 | Ishiguro ............. A61B 1/122 600/159 |
| 5,888,192 | A | 3/1999 | Heimberger |
| 6,288,351 | B1 * | 9/2001 | Bruntz ............... H01H 3/10 200/11 R |
| 6,599,265 | B2 | 7/2003 | Bon |
| 6,656,111 | B2 | 12/2003 | Fujii et al. |
| 6,673,012 | B2 | 1/2004 | Fujii et al. |
| 6,821,282 | B2 | 11/2004 | Perry et al. |
| 7,510,107 | B2 | 3/2009 | Timm et al. |
| 7,588,176 | B2 | 9/2009 | Timm et al. |
| 7,633,837 | B2 | 12/2009 | Daout |
| 7,731,072 | B2 | 6/2010 | Timm et al. |
| 7,735,396 | B2 | 6/2010 | Ishikawa et al. |
| 7,926,379 | B2 | 4/2011 | Gutmann et al. |
| 8,042,423 | B2 | 10/2011 | Bannier et al. |
| 8,048,025 | B2 | 11/2011 | Barenboym et al. |
| 8,052,636 | B2 | 11/2011 | Moll et al. |
| 8,257,303 | B2 | 9/2012 | Moll et al. |
| 8,286,845 | B2 | 10/2012 | Perry et al. |
| 8,302,507 | B2 | 11/2012 | Kanai |
| 8,578,808 | B2 | 11/2013 | Koitabashi |
| 8,808,168 | B2 | 8/2014 | Ettwein et al. |
| 8,845,521 | B2 | 9/2014 | Maruyama |
| 8,904,894 | B2 | 12/2014 | Geiser |
| 8,911,362 | B2 | 12/2014 | Kaneko |
| 9,044,135 | B2 | 6/2015 | Ishii et al. |
| 9,044,138 | B2 | 6/2015 | Sjostrom et al. |
| 9,057,421 | B2 | 6/2015 | Ishikawa et al. |
| 9,155,865 | B2 | 10/2015 | Golden et al. |
| 9,237,837 | B2 | 1/2016 | Omoto et al. |
| 9,360,098 | B2 | 6/2016 | Roopnarine |
| 9,394,985 | B2 | 7/2016 | Kobayashi et al. |
| 9,457,168 | B2 | 10/2016 | Moll et al. |
| 9,534,681 | B2 | 1/2017 | Ishikawa |
| 9,545,253 | B2 | 1/2017 | Worrell et al. |
| 9,833,131 | B2 | 12/2017 | Golden et al. |
| 9,949,623 | B2 | 4/2018 | Lang et al. |
| 10,085,623 | B2 | 10/2018 | Osaki |
| 10,197,153 | B2 | 2/2019 | Dumanski et al. |
| 10,203,022 | B2 | 2/2019 | Atmur et al. |
| 10,238,271 | B2 | 3/2019 | Haraguchi |
| 11,786,112 | B2 | 10/2023 | Nielsen et al. |
| 2001/0037051 | A1 | 11/2001 | Fujii et al. |
| 2002/0019591 | A1 | 2/2002 | Bon |
| 2002/0094232 | A1 * | 7/2002 | Lipp ............. F16D 1/108 403/329 |
| 2002/0099266 | A1 | 7/2002 | Ogura et al. |
| 2004/0010245 | A1 * | 1/2004 | Cerier ............. A61B 17/0057 606/1 |
| 2004/0015054 | A1 * | 1/2004 | Hino ............. G02B 23/2476 600/146 |
| 2009/0149709 | A1 | 6/2009 | Koitabashi |
| 2009/0247828 | A1 | 10/2009 | Watanabe et al. |
| 2011/0118550 | A1 | 5/2011 | Tulley |
| 2011/0144440 | A1 * | 6/2011 | Cropper ............. A61B 17/3421 600/203 |
| 2011/0208001 | A1 * | 8/2011 | Haeckl ............. A61B 1/0051 600/125 |
| 2012/0277535 | A1 | 11/2012 | Hoshino |
| 2013/0204096 | A1 | 8/2013 | Ku et al. |
| 2013/0296848 | A1 | 11/2013 | Allen et al. |
| 2014/0058323 | A1 | 2/2014 | Hoshino |
| 2014/0142389 | A1 | 5/2014 | Lim et al. |
| 2014/0296640 | A1 | 10/2014 | Hoshino |
| 2014/0343489 | A1 | 11/2014 | Lang et al. |
| 2015/0057537 | A1 * | 2/2015 | Dillon ............. A61B 1/0014 600/113 |
| 2015/0359415 | A1 * | 12/2015 | Lang ............. A61M 25/0133 600/141 |
| 2016/0067457 | A1 | 3/2016 | Selkee |
| 2018/0132899 | A1 | 5/2018 | SooHoo |
| 2019/0029498 | A1 | 1/2019 | Mankowski et al. |
| 2019/0035440 | A1 | 1/2019 | Yuan et al. |
| 2019/0209205 | A1 | 7/2019 | Nishio |
| 2019/0313884 | A1 | 10/2019 | Isobe |
| 2019/0350440 | A1 | 11/2019 | Leong et al. |
| 2021/0338049 | A1 | 11/2021 | Christensen |
| 2021/0338051 | A1 | 11/2021 | Nielsen et al. |

FOREIGN PATENT DOCUMENTS

| | | | |
|---|---|---|---|
| EP | 2594307 | A1 | 5/2013 |
| EP | 2692227 | A1 | 2/2014 |
| EP | 2692277 | A1 | 2/2014 |
| EP | 2594307 | B1 | 9/2016 |
| EP | 2692227 | B1 | 8/2018 |
| JP | 09-038028 | A | 2/1997 |
| JP | 2005-160790 | A | 6/2005 |
| WO | 2008/023965 | A1 | 2/2008 |
| WO | 2014/186519 | A2 | 11/2014 |
| WO | 2018/022402 | A1 | 2/2018 |
| WO | 2018/022418 | A2 | 2/2018 |
| WO | 2018/131305 | A1 | 7/2018 |
| WO | 2021/213600 | A1 | 10/2021 |

OTHER PUBLICATIONS

Extended European Search Report issued in EP20172237.8, mailed Oct. 19, 2020, 9 pages.
Extended European Search Report issued in EP20172238.6, mailed Oct. 26, 2020, 9 pages.
Extended European Search Report issued in EP20172242.8, mailed Oct. 12, 2020, 8 pages.
Industrial conical gear, cogwheel, available at Dreamstime.com, website copyright 2000-2019.
Jain et al., "Micromanipulator: Effectiveness in Minimally Invasive Neurosurgery," Minim Invasive Neurosurg 2003; 46(4): 235-239.
Jarrahy et al., "A new powered endoscope holding arm for endoscopic surgery of the cranial base," Minim Invasive Neurosurg 2002, 45(3): 189-192.
Lerner, "A Passive Seven Degree of Freedom Postitioning Device for Surgical Robots and Devices," dissertation submitted to the Johns Hopkins University, Baltimore, Maryland, 1998.
Poels, Design of the Frame and Arms of a Master for Robotic Surgery, Traineeship report, Technische Universiteit Eindhoven, Department of Mechanical Engineer, Control Systems Technology Group, Jul. 2007.
Office Action in related U.S. Appl. No. 17/241,882 dated Dec. 23, 2022, 12 pages.
Final Office Action received for U.S. Appl. No. 17/239,372 dated Nov. 30, 2023, 22 pages.

(56) References Cited

OTHER PUBLICATIONS

Office Action received for European Patent Application No. 20172237.8 dated Jan. 22, 2024, 5 pages.
Office Action received for European Patent Application No. 20172238.6 dated Jan. 16, 2024, 5 pages.

* cited by examiner

ENDOSCOPE CONTROL SYSTEM

CROSS-REFERENCE TO RELATED APPLICATIONS

The present application claims priority to and the benefit of European Patent Application Nos. 20172237.8 and 20172238.6, filed Apr. 30, 2020, which are incorporated by reference herein in their entirety.

TECHNICAL FIELD

The present disclosure relates to insertable medical vision devices, such as, but not limited to, endoscopes, in particular disposable insertion endoscopes, such as duodenoscopes, gastroscopes, and colonoscopes. More specifically, the present disclosure relates to endoscope control systems comprising control wheels connected to associated wire drums for connection to steering wires, whereby rotation of the control wheels controls a bending operation of a tip of the endoscope.

BACKGROUND

Endoscopes are typically equipped with a light source and a vision receptor including a vision or image sensor. Provided that enough light is present, it is possible for the operator to see where the endoscope is steered and to set the target of interest once the tip has been advanced thereto.

Endoscopes typically comprise an elongated insertion tube with a handle at the proximal end, as seen from the operator, and visual inspection means, such as a built-in camera including a vision sensor, at a distal end of the elongated insertion tube. This definition of the terms distal and proximal, i.e. "proximal" being the end closest to the operator and "distal" being the end remote from the operator, as used herein for endoscopes in general, is adhered to in the present specification. Electrical wiring for the camera and other electronics, such as one or more LEDs accommodated in the tip part at the distal end, runs along the inside of the elongated insertion tube from the handle to the tip part. A working or suction channel may run along the inside of the insertion tube from the handle to the tip part, e.g. allowing liquid to be removed from the body cavity or allowing for insertion of surgical instruments or the like into the body cavity. The suction channel may be connected to a suction connector, typically positioned at a handle at the proximal end of the insertion tube.

To be able to maneuver the endoscope inside the body cavity, the distal end of some endoscopes comprises a bendable distal tip, which may be bendable in one, e.g. an up/down dimension, or two dimensions, e.g. an up/down dimension and a left/right dimension. The bendable tip often comprises a bending section with increased flexibility, e.g. achieved by articulated segments of the bending section. The maneuvering of the endoscope inside the body is typically done by tensioning or slacking steering wires also running along the inside of the elongated insertion tube from the tip part through the remainder of articulated segments to a control system or control mechanism positioned in or forming part of the handle.

An endoscope control system for performing a bending operation in two dimensions is known from WO2018022418A2. This control system includes two control wheels connected to associated wire drums for connection to associated steering wires of the endoscope, whereby rotation of the control wheels controls the bending operation in two dimensions.

U.S. Pat. No. 4,461,282 discloses another endoscope control system including two control wheels.

SUMMARY OF EMBODIMENTS OF THE DISCLOSURE

A first aspect of the present disclosure relates to an endoscope control system for performing a bending operation in a disposable insertion endoscope, the endoscope control system comprising:

an endoscope handle with a handle housing;
a first control wheel connected to a first wire drum for connection to a first steering wire of the endoscope, whereby rotation of the first control wheel relative to the handle housing about an axis of rotation controls the bending operation in a first dimension, the first control wheel comprising a bearing surface;
a second control wheel connected to a second wire drum for connection to a second steering wire of the endoscope, whereby rotation of the second control wheel relative to the handle housing about the axis of rotation controls the bending operation in a second dimension, the second control wheel comprising an outer bearing surface positioned farther from the axis of rotation than the bearing surface of the first control wheel; and
an outer bearing element forming part of or being rotationally fixed to the handle housing, the outer bearing element comprising an inner bearing surface positioned farther from the axis of rotation than the outer bearing surface of the second control wheel, the inner bearing surface of the outer bearing element abutting the outer bearing surface of the second control wheel so that rotation of the second control wheel is at least partly borne on the outer bearing element.

When the outer bearing element of the endoscope control system is provided on an outside of the second control wheel, a wall thickness of the outer bearing element may be less or not at all decisive for a total cross-sectional extent of the part of the control system, which does not include the handle. Therefore, it may be possible to allow this wall thickness to be larger, allowing for manufacture of the outer bearing element in a cheaper and/or less rigid and/or more environmentally friendly material, such as a plastic polymer, such as polyoxymethylene (POM). When the below described inner bearing element is positioned between the inner and outer control wheels, this may not apply to the inner bearing element described below, which may make it advantageous to manufacture the inner bearing element of a more rigid material and with a smaller wall thickness, such as polycarbonate (PC). When the second control wheel is borne on the outer bearing element, and thus not on an inner bearing element, less force is exerted on the inner bearing element, which may allow for the use of an inner bearing element (for which the cross-sectional extent may be more important) of a less rigid material and/or of smaller wall thickness, potentially resulting in a smaller cross-sectional extent or diameter. When the outer bearing element can be manufactured in a cheaper and/or less rigid and/or more environmentally friendly material, such as a plastic polymer, it may become advantageous to manufacture the outer bearing element in one piece with and/or of the same material as the handle housing, potentially saving material costs and/or weight and/or easing manufacture.

The endoscope control system can alternatively be denoted an endoscope bending operation apparatus.

The control system may be positioned on or in, or may form part, of an endoscope handle of the endoscope, see also further below.

The first and/or second control wheels and/or the outer bearing element and/or the first and/or second wire drums may form part of the endoscope handle. The same is the case for the inner bearing element described below.

The first control wheel may be positioned coaxially with the second control wheel and/or with the outer bearing element and/or the inner bearing element and/or the first and/or second wire drums.

The handle housing may be or comprise a handle frame and/or may be manufactured of a plastic material, potentially a plastic polymer material and/or an artificial resin. One or both control wheels or at least the sleeves thereof described below, and/or one or both wire drums may be manufactured from one or more plastics or a plastics material, such as POM. The entire control system may be manufactured of one or more plastics or plastic materials or plastic polymer materials or artificial resins, and/or the control system does not include any metal. Any one of the plastic materials mentioned herein may be a plastic polymer material which comprises or consists of one or more of PC, polypropylene (PP), acrylonitrile butadiene styrene (ABS), polyethylene (PE), polyamide (PA), polyurethane (PU), polystyrene (PS), polylactic acid (PLA), polyvinyl chloride (PVC), polyoxymethylene (POM), polyester, polyethylene terephthalate (PET), and acrylic (PMMA). The polymer may be a copolymer of one or more monomers of the latter materials.

Rotation of the control wheels may occur relative to the frame. The handle housing or the frame may be a handle shell or a housing shell. The frame and/or the housing may be manufactured of a rigid material, such as a rigid plastic polymer. The handle housing may be a handle shell.

The first and/or second wire drums may be a pulley/pulleys. The first and second steering wires may form part of the control system and may be attached to the first and the second drum, respectively, and/or may be wound up or woundable on these, respectively.

The axis of rotation may be an axis of rotation of also the first and/or second wheel sleeves described below.

The axis of rotation may be a center axis of the first and/or second control wheel and/or of the first and/or second wheel handles described below and/or of the first and/or second wheel sleeves as described below and/or of the control system and/or of the outer bearing element and/or of the inner bearing element described below and/or of the center shaft described below.

The first and second control wheels may comprise first and second control handles, respectively, of which one or both may comprise finger depressions. The second wheel handle may be positioned between the handle housing and the first wheel handle. A first wheel sleeve connecting the first wheel handle to the first wire drum may extend through, potentially through center holes of, the second wheel handle and/or through a second wheel sleeve, which connects the second wheel handle to the second wire drum, and/or through, potentially through a center opening of, the second wire drum.

The second wire drum may be positioned between the first wire drum and the second control wheel.

The first control wheel may be an inner control wheel and/or may be positioned closer to the handle housing than the second control wheel and/or may control a bendable tip of the endoscope in an up/down dimension. The second control wheel may be an outer control wheel and/or may control a bendable tip of the endoscope in a left/right dimension.

The first control wheel may comprise a first wheel sleeve and potentially a first wheel handle, the first wheel sleeve connecting the first wheel handle to the first wire drum, the first wheel sleeve comprising the bearing surface of the first control wheel. Similarly, the second control wheel may comprise a second wheel sleeve and potentially a second wheel handle, the second wheel sleeve connecting the second wheel handle to the second wire drum, the second wheel sleeve comprising the outer bearing surface of the second control wheel. The second wheel sleeve may encompass at least part of the first wheel sleeve. The first and/or second wheel sleeves may each be cylindrical or circular cylindrical and/or may be embodied as cylinder shells and/or may be hollow. The second wheel sleeve may be positioned to be coaxial with the first wheel sleeve. The inner bearing element may be an inner bearing sleeve and may be the only element positioned between the first wheel sleeve and the second wheel sleeve.

The outer bearing element may be of the same material as or of a material different from, potentially of higher rigidity and/or stiffness, such as a metallic material, than that of the handle housing. The outer bearing element may be or include a potentially cylindrical outer bearing sleeve having a wall or a cylinder shell with a wall thickness of less than one fifth, one sixth, one seventh, one eighth, one ninth, or one tenth of a diameter or a cross-sectional extent of the outer bearing sleeve. The wall thickness of the outer bearing sleeve may be more than one twentieth, one fifteenth, one twelfth, one tenth, one ninth, one eighth, or seventh, or one sixth of a diameter or a cross-sectional extent of the outer bearing sleeve.

The control system may further comprise the inner bearing element forming part of or being rotationally fixed to the handle housing. The inner bearing element may be of a material different from, potentially of higher rigidity and/or stiffness, than that of the handle housing. The inner bearing element may be or include a potentially cylindrical inner bearing sleeve having a wall or a cylinder shell with a wall thickness of less than one twentieth, one thirtieth, one fortieth, or one fiftieth of a diameter or a cross-sectional extent of the outer bearing sleeve. The wall thickness of the inner bearing sleeve may be less than, potentially less than half of, a quarter of, or an eight of that of the outer bearing sleeve.

The first and second control wheels may be connected to first and second wire drums for connection to a steering wire of the endoscope, whereby rotation of the control wheel controls the bending operation.

The control system may, for one or both control wheels, comprise a brake system, which may include a brake handle, or a similar activation device or activation means, movement of which moves a brake between a braking position and a released position. Such movement may be a rotation, potentially about a rotation axis of the control wheel. In the braking position, rotation of the associated control wheel may be braked or hindered. In the releasing position, rotation of the associated control wheel may be allowed.

Any one of or all of the above-mentioned elements of the control system, potentially except for steering wires and/or parts of the brake system may be manufactured from plastic polymer(s).

The second control wheel may be positioned coaxially with and potentially axially shifted in relation to the first control wheel. A diameter or a cross-sectional dimension of the two control wheels may be different from each other, potentially so that an outer one of the two control wheels has a smaller diameter or smaller cross-sectional dimension.

In an embodiment of the control systems according to the present disclosure, the inner bearing surface of the outer bearing element and the outer bearing surface of the second control wheel each extends circumferentially about the axis of rotation.

In another embodiment, the inner bearing surface of the outer bearing element and the outer bearing surface of the second control wheel each includes at least two bearing surface parts, which are positioned at an axial distance from each other.

Hereby, more stability of the rotational movement may be provided.

The bearing surface parts may alternatively be denoted bearing interfaces.

The at least two bearing surface parts may consist of two or three bearing surface parts.

Two of the at least two bearing surface parts may, respectively, be positioned at upper and lower parts or ends of the second wheel sleeve and the outer bearing sleeve. A third bearing surface part or more bearing surface parts may be provided between the two bearing surface parts positioned at upper and lower parts or ends of the second wheel sleeve and the outer bearing sleeve.

Similarly, the inner bearing surface of the inner bearing element and the outer bearing surface of the first control wheel may each include two bearing surface parts, which are positioned at an axial distance from each other. And, similarly, the two bearing surface parts may, respectively, also here be positioned at upper and lower parts or ends of the first wheel sleeve and the inner bearing sleeve.

In another embodiment, the outer bearing element is in one piece with the handle housing.

The outer bearing element may be integral with and/or molded in one piece with the handle housing.

Alternatively, the outer bearing element is provided separately from and is fixed to the handle housing.

In another embodiment, the first control wheel comprises a first wheel handle and a first wheel sleeve, the first wheel sleeve connecting the first wheel handle to the first wire drum, the first wheel sleeve comprising the bearing surface of the first control wheel, wherein the second control wheel comprises a second wheel handle and a second wheel sleeve, the second wheel sleeve connecting the second wheel handle to the second wire drum, the second wheel sleeve comprising the outer bearing surface of the second control wheel, and wherein the second wheel sleeve encompasses at least part of the first wheel sleeve.

The first and/or second wheel sleeves may each be cylindrical or circular cylindrical and/or may be embodied as cylinder shells and/or may be hollow.

The second wheel sleeve may be positioned to be coaxial with the first wheel sleeve.

The inner bearing element or an inner bearing sleeve may be the only element positioned between the first wheel sleeve and the second wheel sleeve.

In a development of the above embodiment, the outer bearing element is an outer bearing sleeve that encompasses at least part of the second wheel sleeve.

Similarly, the inner bearing element may be or comprise an inner bearing sleeve that encompasses at least part of the first wheel sleeve.

The outer bearing sleeve may encompass at least part of the second wheel sleeve, which may again encompass at least part of the inner bearing sleeve, which may again encompass at least part of the first wheel sleeve. The second wheel sleeve may be positioned between and be rotational relative to the inner and outer bearing sleeves, which may each be static relative to the handle housing. The second wheel sleeve may be positioned between and be rotational relative to the inner and outer bearing sleeves, the second wheel sleeve being rotationally borne or supported on the outer bearing sleeve. The first wheel sleeve may be positioned on an interior side of the inner bearing sleeve and similarly be rotational relative to the inner and outer bearing sleeves, which may both be static relative to the handle housing.

The outer bearing element may alternatively comprise an outer bearing sleeve that encompasses at least part of the second wheel sleeve.

Another embodiment further comprises an inner bearing element forming part of or being rotationally fixed to the handle housing, the inner bearing element comprising an inner bearing surface positioned farther from the axis of rotation than the outer bearing surface of the second control wheel, the inner bearing surface of the bearing element abutting the outer bearing surface of the control wheel so that rotation of the second control wheel is at least partly borne on the inner bearing element.

The second control wheel or a second wheel sleeve thereof may also be rotationally borne or supported on the inner bearing element, which may be or comprise an inner bearing sleeve, the inner bearing element comprising an outer bearing surface positioned closer to the axis of rotation than an inner bearing surface of the first control wheel, the outer bearing surface of the inner bearing element abutting an inner bearing surface of the second control wheel so that rotation of the first control wheel is at least partly borne on the inner bearing element.

The first control wheel or a first wheel sleeve thereof may be rotationally borne or supported on the inner bearing element, which may be or comprise an inner bearing sleeve, the inner bearing element comprising an inner bearing surface positioned farther from the axis of rotation than an outer bearing surface of the first control wheel, the inner bearing surface of the inner bearing element abutting an outer bearing surface of the first control wheel so that rotation of the first control wheel is at least partly borne on the inner bearing element.

Alternatively, the control system further comprises a center shaft, the first control wheel or a first wheel sleeve thereof instead, or in addition, being rotationally borne or supported on the center shaft, the center shaft forming part of or being rotationally fixed to the handle housing, the center shaft comprising an outer bearing surface positioned closer to the axis of rotation than an inner bearing surface of the first control wheel or a first wheel sleeve thereof, the outer bearing surface of the center shaft abutting the inner bearing surface of the first control wheel so that rotation of the first control wheel is at least partly borne on the center shaft. the first wheel sleeve may encompass at least part of the center shaft.

In the embodiment where the first control wheel is borne on the inner bearing element, the center shaft may also be provided.

The inner bearing element may generally be fixed to the, or to other parts of the, handle housing by means of screws and/or a snap connection.

In another embodiment, the inner bearing element separates at least part of the first and second control wheels from each other so that rotation of the control wheels is mutually separated from each other.

The inner bearing element may separate at least part of the first and second wheel sleeves from each other.

Alternatively, or in addition, the two control wheels, or wheel sleeves thereof, may be located at a distance from each other and/or not be in contact with each other.

In another embodiment, the inner bearing element is provided separately from and is fixed to the handle housing.

Alternatively, the inner bearing element is in one piece with and/or integral with, and/or molded in one piece with the handle housing.

In another embodiment, the outer bearing element is an outer bearing sleeve that projects from a surface of the handle housing toward a wheel handle of the second control wheel.

The outer bearing sleeve may be a hollow cylinder.

Alternatively, or in addition, the inner bearing element may be or comprise an inner bearing sleeve, which may also be a hollow cylinder, that projects from a surface of the handle housing toward a wheel handle of the second control wheel.

In another embodiment, the second control wheel comprises a second wheel handle and a second wheel sleeve, the second wheel sleeve connecting the second wheel handle to the second wire drum, the second wheel sleeve comprising an inner part in one piece with the second wheel handle, the inner part of the second wheel sleeve being fixed to an outer part of the second wheel sleeve, the outer part of the second wheel sleeve being in one piece with the second wire drum, and wherein the outer bearing surface of the second control wheel is an outer surface of the outer part of the of the second wheel sleeve.

Alternatively, or in addition, the first control wheel comprises a first wheel handle and a first wheel sleeve, the first wheel sleeve connecting the first wheel handle to the first wire drum, the first wheel sleeve comprising an outer part in one piece with the first wheel handle, the outer part of the first wheel sleeve being fixed to an inner part of the first wheel sleeve, the inner part of the first wheel sleeve being in one piece with the first wire drum, and wherein, potentially, the outer bearing surface of the first control wheel is an outer surface of the inner part of the of the first wheel sleeve.

In another embodiment, the outer bearing element comprises a stop surface associated with a stop surface of the second control wheel so that when the second control wheel is rotated in a direction of rotation to an end position, mutual abutment of the stop surfaces prevents the second control wheel from rotating farther in that direction of rotation.

The outer bearing element may comprise a further stop surface associated with a further stop surface of the second control wheel so that when the second control wheel is rotated in a direction of rotation opposite to the one defined above to an opposite end position, mutual abutment of the further stop surfaces prevents the second control wheel from rotating farther in that opposite direction of rotation.

The inner bearing element may similarly comprise a stop surface associated with a stop surface of the first control wheel so that when the first control wheel is rotated in a direction of rotation to an end position, mutual abutment of the stop surfaces prevents the first control wheel from rotating farther in that direction of rotation. The inner bearing element may similarly comprise a further stop surface associated with a further stop surface of the first control wheel so that when the first control wheel is rotated in a direction of rotation opposite to the latter one to an opposite end position, mutual abutment of the further stop surfaces prevents the first control wheel from rotating farther in that opposite direction of rotation.

Hereby, restriction of rotation of one or both control wheels may achieved, which may accordingly restrict bending of a tip of the endoscope between bended end positions in the first or both the first and the second dimensions.

In another embodiment, the outer bearing element comprises an outer bearing sleeve having a wall with a wall thickness of more than one twentieth of a diameter or a cross-sectional extent of the outer bearing sleeve, and wherein the control system further comprises an inner bearing element forming part of or being rotationally fixed to the handle housing, the inner bearing element comprising an inner bearing sleeve having a wall with a wall thickness of less than one thirtieth of a diameter or a cross-sectional extent of the outer bearing sleeve.

In another aspect, the present disclosure involves an endoscope comprising a control system according to any one of the above embodiments and/or options.

The endoscope may further comprise an endoscope handle at the proximal end thereof, and/or visual inspection means, such as a built-in camera including a vision sensor, at a distal tip. Electrical wiring for the camera and other electronics, such as one or more LEDs accommodated in the tip part at the distal end, may run along the inside of the elongated insertion tube from the endoscope handle to a PCB or an FPC at the distal tip. A working or suction channel may run along the inside of the insertion tube from the handle to the tip part, e.g. allowing liquid to be removed from the body cavity or allowing for insertion of surgical and/or sampling instruments or the like into the body cavity. The suction channel may be connected to a suction connector, typically positioned at a handle at the proximal end of the insertion tube.

In some embodiments of the endoscope, the endoscope further comprises a distal tip or tip part that comprises a bending section connected to the steering wire(s) so that the control system can activate a bending operation of the bending section via the steering wire(s).

The bending section may be bendable in one or two dimensions, e.g. an up/down dimension and a left/right dimension. The bendable tip may comprise a bending section with increased flexibility, e.g. achieved by articulated segments of the bending section as are known in the art. The steering wire(s) may run along the inside of an elongated insertion tube from the tip through the bending section to the control system positioned in or forming part of the endoscope handle.

The endoscope may be a disposable insertion endoscope. The endoscope may include one or more features as described herein in the above, including the features of endoscopes described in the above introduction to this description, and in connection with the description of the methods and tip parts according to the present disclosure.

The endoscope may comprise an elongated insertion tube with a handle at the proximal end. A tip or tip part may be positioned at the distal end of the elongated insertion tube. The tip may further comprise a bending section positioned between the tip and the elongated insertion tube. The bending section may be configured to be articulated to maneuver the endoscope inside a body cavity.

The endoscope may be a duodenoscope, a gastroscope, or a colonoscope.

An embodiment of the endoscope further comprises the first and second steering wires and a distal tip or tip part that comprises a bending section connected to the first and second steering wires so that the control system can activate the bending operation of the bending section via the steering wires.

A person skilled in the art will appreciate that any one or more of the above aspects of this disclosure and embodiments thereof may be combined with any one or more of the other aspects and embodiments thereof.

BRIEF DESCRIPTION OF THE DRAWINGS

In the following, non-limiting exemplary embodiments will be described in greater detail with reference to the drawings, in which.

DETAILED DESCRIPTION

In this disclosure, the term "to accommodate" may additionally or alternatively be defined as "to house" or "to enclose" or "to surround".

In this specification, the terms "integrally" or "integrally provided" or "integrally comprising", "in one piece", or similar may be defined as the associated features forming an integral part of a whole; and/or are in one piece, potentially molded in one piece; and/or are substantially inseparable by hand. When a first element forms part of a second element, this may involve that the first element is provided integrally with or in one piece with the second element.

As mentioned, in this specification, the term "proximal" may be defined as being closest to an operator of the endoscope, and the term "distal" as being remote from the operator. The term "proximal-distal" may be defined as extending between these two extremes, in the present case proximal-distal may extend along a center axis of the tip part extending between a proximal extremity of the proximal end of the tip part and a distal extremity of the distal end of the tip part.

In this specification, an endoscope may be defined as a device adapted for viewing body cavities and/or channels of a human and/or animal body. The endoscope may for instance be a flexible or steerable endoscope. The endoscope may be a duodenoscope or a ureteroscope, a gastroscope, or a colonoscope.

Figure 1:
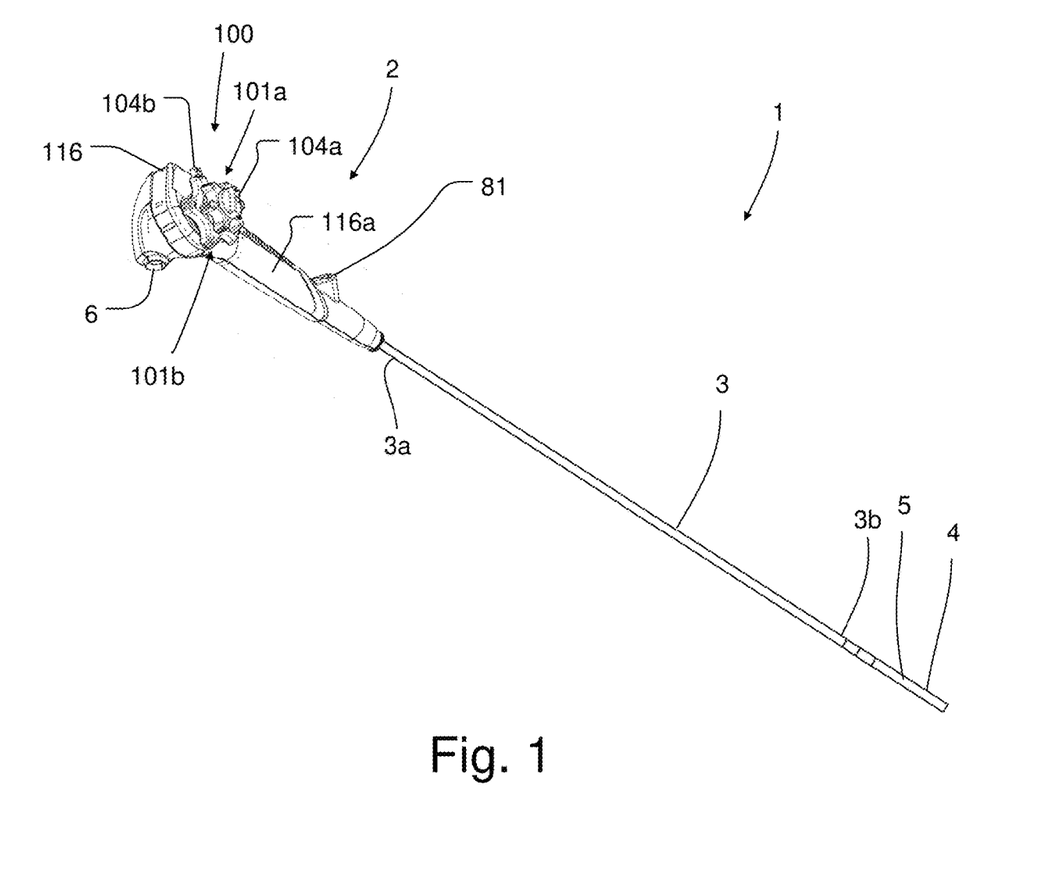
FIG. 1 shows a perspective view of an endoscope including control system according to the present disclosure.
Figure 2:
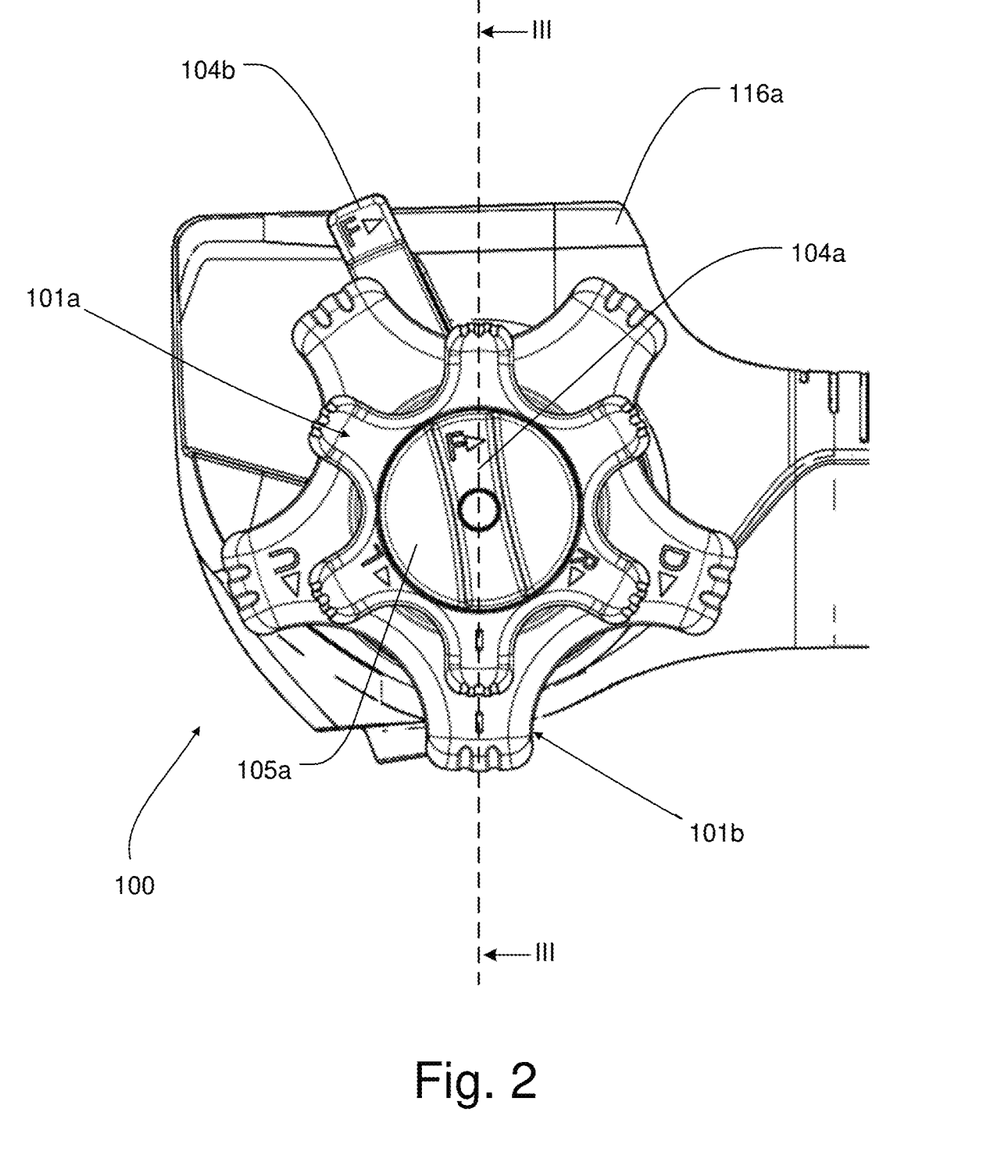
FIG. 2 shows a top view of the control system of FIG. 1.

FIG. 1 shows a disposable insertion endoscope 1 with a control system 100, an elongated insertion tube 3, and an endoscope handle 2 at a proximal end 3a of the elongated insertion tube 3. The endoscope handle includes a handle housing 116

In a known manner, an endoscope tip 4 is positioned at a distal end 3b of the elongated insertion tube 3, the tip 4 comprising a bending section 5 positioned between the tip 4 and the elongated insertion tube 3. The endoscope handle 2 comprises the endoscope control system 100, the endoscope control system 100 being for performing a bending operation of the disposable insertion endoscope 1.

In a known manner, the bending section 5 is connected to steering wires 102k, 102l, which extend from the control system 100 through the tube 3 to allow the control system 100 to activate a two-dimensional bending operation of the bending section 5 via the steering wires. The bending section 5 is configured to be articulated to maneuver the endoscope 1 inside a body cavity (not shown). The bending section 5 is bendable in two dimensions, i.e. an up/down dimension and a left/right dimension.

The bending section 5 has increased flexibility achieved by articulated segments of the bending section 5 as is known in the art. The steering wires run along the inside of the elongated insertion tube 3 from the tip 4 through the bending section 5 to the endoscope control system 100. Still in a known manner, the maneuvering of the endoscope 1 inside the body can be carried out by tensioning or slacking the steering wires by means of the control system 100.

Still in a known manner, the distal tip 4 has a not shown built-in camera including a vision sensor. Not shown electrical wiring for the camera and potential other electronics, such as one or more LEDs accommodated in the tip part 4, run along the inside of the elongated insertion tube 3 from the endoscope handle 2 to a PCB or an FPC at or in the distal tip 4. A not shown suction/working channel runs along the inside of the insertion tube 3 from the handle 2 to the tip part 4, e.g. allowing liquid to be removed from the body cavity or allowing for insertion of a surgical instrument and/or a sampling instrument or other instruments (not shown) into the body cavity. The suction channel is connected to a suction connector 6 positioned at the proximal end of the handle 2. A sampling connector 81 is positioned at the distal end of the handle 2.

Referring to FIGS. 1 to 7, the control system 100 comprises a first control wheel 101 connected to a first wire drum 102a for connection to a steering wire of the endoscope 1, whereby rotation of the first control wheel 101 controls the bending operation in one dimension by rotating the wire drum 102a to, in a known manner, activate the steering wire, the steering wire being connected to the wire drum 102a.

The first control wheel 101 comprises a first shaft/sleeve 102e which connects a first wheel handle 101c of the first control wheel 101 to the first wire drum 102a for connection to a first steering wire 102k of the endoscope 1. The first shaft 102e comprises an outer bearing surface 102i. The first shaft 102e and the first wire drum 102a are provided as a one-piece element denoted a first shaft unit 102c. The first wheel handle 101c and the first central part 102g are provided as a one-piece element denoted a first control wheel unit 101a. Hereby, rotation of the first control wheel 101 relative to the handle housing 116 about an axis of rotation controls the bending operation in the first dimension.

Referring to FIGS. 1 to 4 and 8 to 10, the control system 100 also comprises a second control wheel 102 similarly connected to a second wire drum 102b for connection to another steering wire of the endoscope 1, whereby rotation of the second control wheel 102 controls the bending operation in another dimension by rotating the wire drum 102b to activate the steering wire, the steering wire being connected to the wire drum 102b.

The second control wheel 102 comprises a second shaft/sleeve 102f which connects a second wheel handle 101d of the second control wheel 102 to the second wire drum 102b for connection to a second steering wire 102l of the endoscope 1. The second shaft 102f and the second wire drum 102b are provided as a one-piece element denoted a second shaft unit 102d. The second shaft/sleeve 102f comprises an outer bearing surface 102j. The second wheel handle 101d and the second central part 102h are provided as a one-piece element denoted a second control wheel unit 101b. Hereby, rotation of the second control wheel 102 relative to the handle housing 116 about the axis of rotation controls the bending operation in a second dimension. The outer bearing surface 102j of the second control wheel 102 is positioned farther from the axis of rotation than the bearing surface 102i of the first control wheel 101.

An outer bearing element 120b is in one piece with a housing frame 116a of the handle housing 116, the outer bearing element 120b comprising an inner bearing surface 120d positioned farther from the axis of rotation than an outer bearing surface 102j of the second control wheel 102, the inner bearing surface 120d of the outer bearing element 120b abutting the outer bearing surface 102j of the second control wheel 102 so that rotation of the second control wheel 102 is at least partly borne on the outer bearing element 120b. The outer bearing element 120b is shaped as a cylindrical sleeve having a wall or a cylinder shell with a wall thickness.

As shown in FIG. 1, the control system 100 is partly positioned in the handle housing 116 to form part of the endoscope handle 2.

Rotation of the control wheels 101, 102 occurs relative to a housing frame 116a, which is a half part of whole housing frame forming the handle housing 116 which when assembled as shown in FIG. 1 comprises another half part as well.

The inner bearing surface 120d of the outer bearing element 120b and the outer bearing surface 102j of the second control wheel 102 each extends circumferentially about the axis of rotation. The inner bearing surface 120d and the outer bearing surface 102j each includes two circumferentially extending bearing surface parts/portions or bearing interfaces 102jbs (see FIGS. 3 and 9), which are positioned at an axial distance from each other. A non-bearing portion 102jnbs is shown between the bearing surface portions. In these interfaces, the surfaces 120d and 102j are in abutment with each other. Hereby, stability of the rotational movement is provided. The bearing surface parts are positioned at upper and lower parts or ends of the second shaft/sleeve 102e and the outer bearing element/sleeve 120b.

Similarly, the inner bearing surface 120c of the inner bearing element 120a and the outer bearing surface 102i of the first control wheel 101 each includes two bearing surface parts, which are similarly positioned at an axial distance from each other.

The outer bearing element 120b is in one piece with the handle frame 116a of the handle housing 116.

The first and second shafts/sleeves are each cylindrical or, rather, slightly conical, and hollow.

The second shaft/sleeve 102f encompasses a part of the first shaft/sleeve 102e. The outer bearing element 120b encompasses part of the second shaft/sleeve 102f. The inner bearing element 120a comprises an inner bearing sleeve or sleeve part 120e that encompasses part of the first shaft/sleeve 102e. The outer bearing element encompasses part of the second shaft/sleeve 102f, which again encompasses part of the sleeve part 120e, which again encompasses part of the first shaft/sleeve 102e.

The second shaft/sleeve 102f is positioned between and is rotational relative to the inner and outer bearing elements 120a, 120b, which are static relative to the handle housing 116, the second shaft/sleeve 102f being rotationally borne or supported on the outer bearing element 120b. The first shaft/sleeve 102e is positioned on an interior side of the inner bearing element 120a and is rotational relative to the inner and outer bearing elements 120a, 120b, which are both static relative to the handle housing 116.

The inner bearing element 120a separates the first and second control wheels 101, 102 from each other so that rotation is mutually separated.

The first shaft/sleeve 102e embodies the first wheel sleeve mentioned above, and the second shaft/sleeve 102f embodies the second wheel sleeve mentioned above.

The first and second wire drums 102a, 102b are positioned inside the assembled handle housing 116.

The first and second wheel handles 101c, 101d are generally circular and comprise conventionally provided finger depressions or cut-outs.

Each of the first and second control wheels 101, 102 comprises a central part 102g, 102h, first and second, respectively, each surrounding a center opening. The central parts 102g, 102h are cylindrical and extend towards the housing frame 106a. The second central part 102h may in other embodiments extend to encompass part of the first central part 102g in the assembled state of the control system 100.

The first and second shafts 102e, 102f are each tubular and each comprises a substantially cylindrical or, rather, slightly conical circumferential wall which provide the associated bearing surfaces 102i, 102j. A diameter of the first shaft 102e is smaller than that of the second shaft 102f.

The axes of rotation of the control wheels 101, 102 are coinciding to form one axis of rotation, which is also a center axis of the control system 100. This axis extends in an assembly direction D in which the different elements of the control system are assembled. The first and second shafts 102e, 102f, the first and second control wheels 101, 102, and the first and second wheel handles 101c, 101d extend coaxially in the assembled control system 100.

Figure 4:
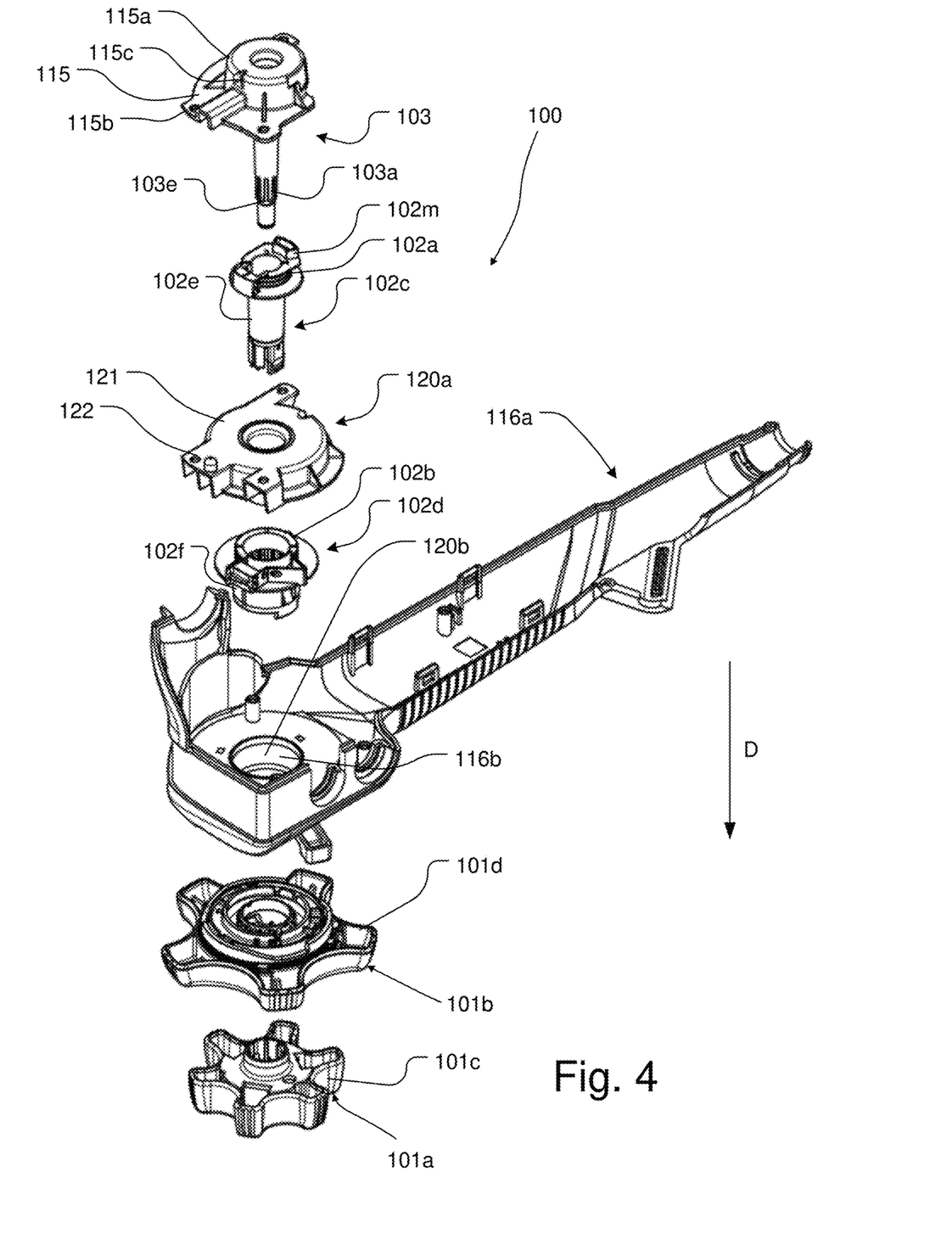
FIG. 4 shows an exploded perspective view of a handle frame and the control system of the endoscope of FIG. 1.
Figures 5, 6, 7:
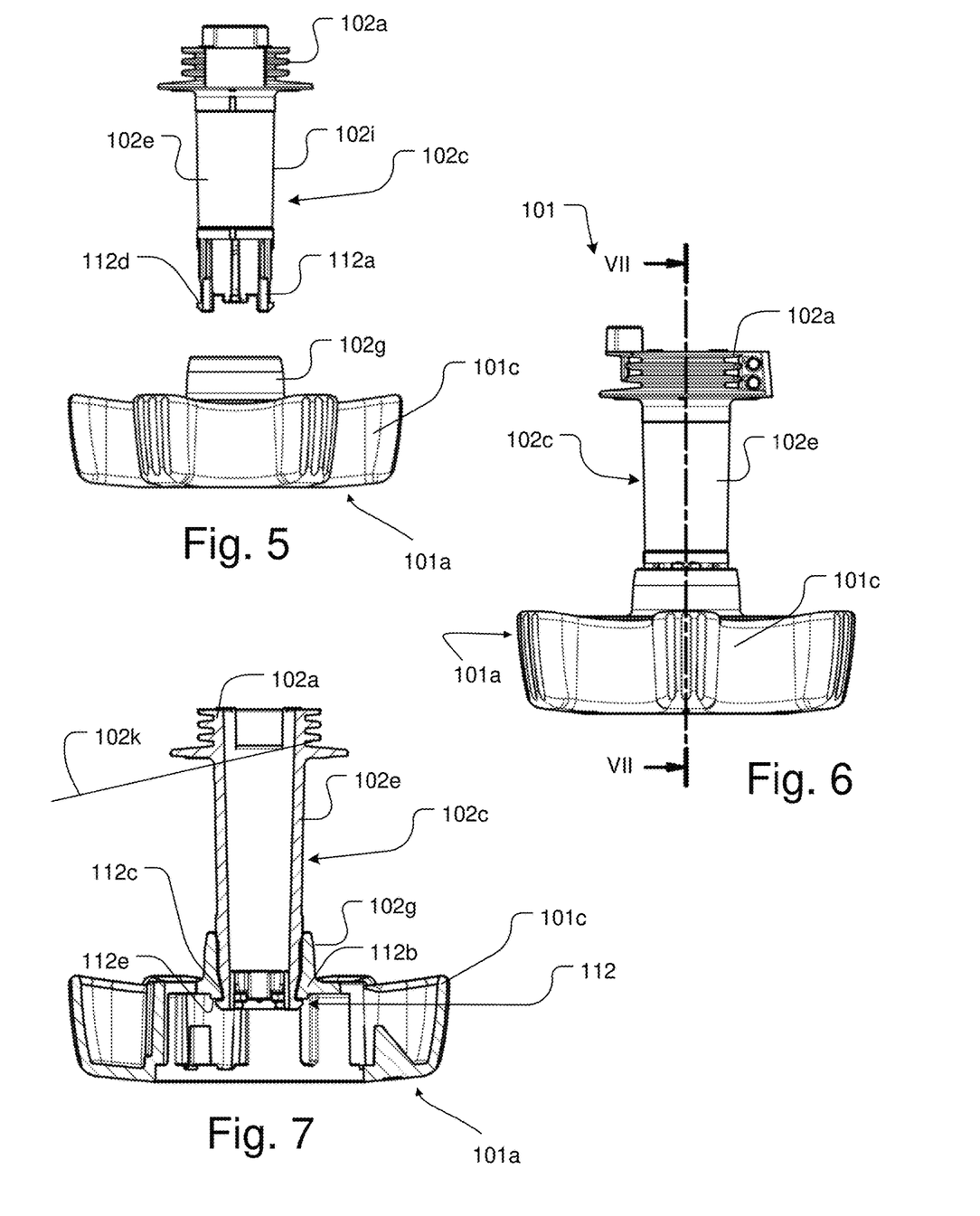
FIG. 5 shows an exploded side view of a first control wheel and a first shaft unit of the control system of FIG. 1.
FIG. 6 shows an exploded side view of the first control wheel and first shaft unit of FIG. 5 in an assembled state and in which the first control wheel and first shaft unit have been turned 180 degrees.
FIG. 7 shows a cross section taken along the line VII-VII in FIG. 6.
Figures 8, 9, 10:
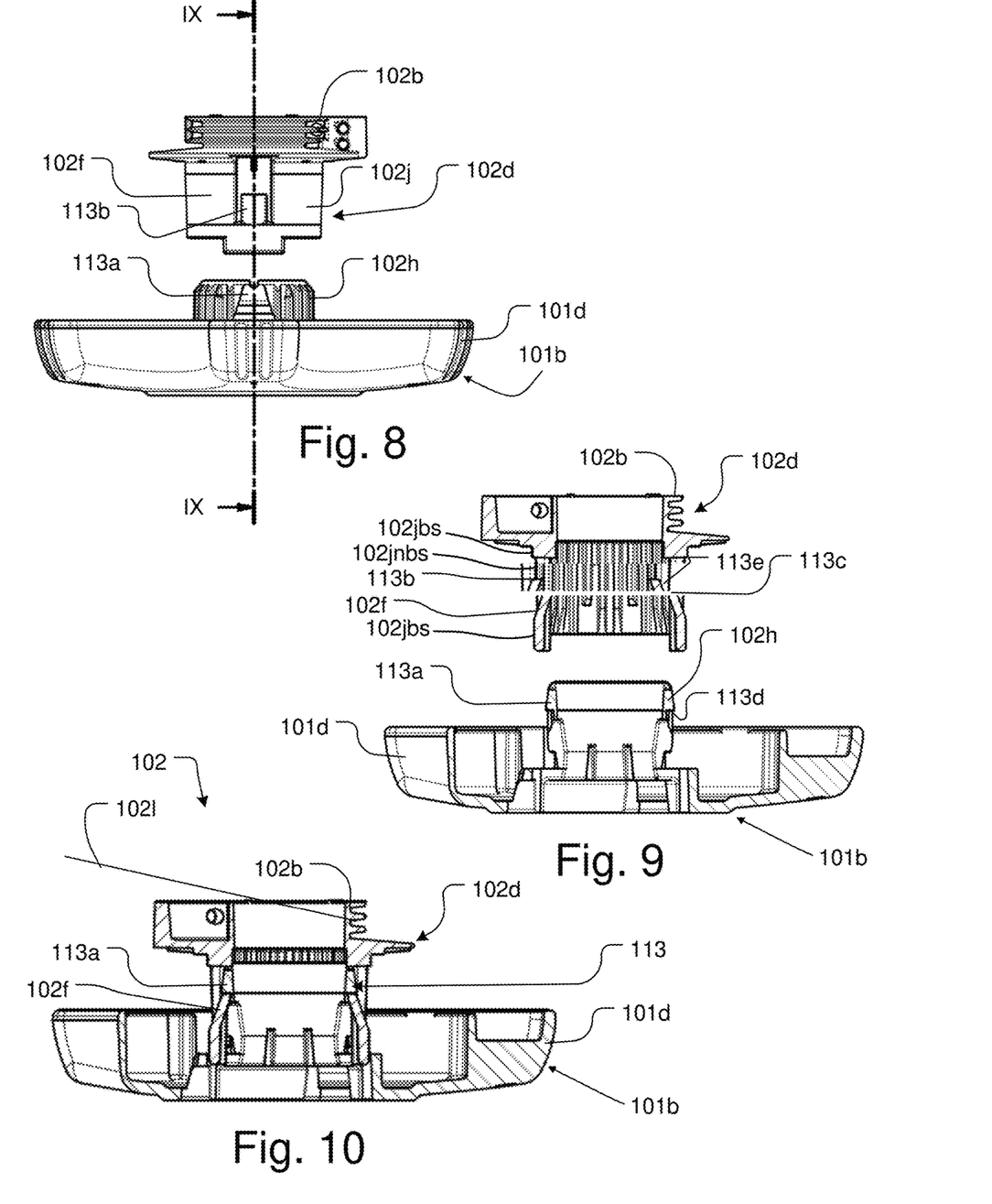
FIG. 8 shows an exploded side view of a second control wheel and a second shaft unit of the control system of FIG. 1.
FIG. 9 shows a cross-sectional view taken along the line IX-IX of FIG. 8.
FIG. 10 shows a view like that of FIG. 9, wherein the second control wheel and second shaft unit are in an assembled state.

As shown in FIG. 4, the first and second wire drums 102a, 102b on the one hand and the first and second wheel handles 101c, 101d on the other hand are positioned on opposite sides of the connection hole 116b of the housing frame 116a. The first wire drum 102a is positioned in extension of the second wire drum 102b and farther from the housing frame 116a or the connection hole 116b than the second wire drum 102b.

The first and second wire drums 102a, 102b are positioned at upper ends of the first and second shafts 102e, 102f, respectively.

The control system 100 further includes a center shaft 103 which extends through a connection hole 116b of the housing frame 116a, the first and second shaft units 102c, 102d, and the center openings of the first and second control wheels 101, 102. The center shaft 103 comprises a connector frame or center shaft frame 115. The connector frame 115 is fixed to the housing frame 116a via the inner bearing element frame 121, see below, after insertion of the center shaft 103. Hereby, the center shaft 103 is fixed to the housing frame 116a. The connector frame 115 extends radially from a shaft part 103a of the center shaft 103 and is positioned within the handle housing 116a in the assembled endoscope 1, see FIG. 3. The connector frame 115 includes a housing 115a including a flange 115b fixed to the housing frame. The housing 115a includes an indentation 115c that operates as stop or stop surface when it contacts a corresponding stop surface 102m on a longitudinally protruding portion of the first shaft unit 102c as it rotates. The protruding portion has an arcuate shape and its length determines the angle of rotation of the first shaft unit 102c.

Similarly, the inner bearing element 120a includes an inner bearing element frame 121 that extends radially from a sleeve part 120e thereof and is positioned within the handle housing 116 in the assembled endoscope 1. The inner bearing element frame 121 is directly fixed to the housing frame 116a, the center shaft frame 115 being directly fixed to the inner bearing element frame 121 by means of screws (not shown) so as to be indirectly fixed to the housing frame 116a. The screws are inserted into screw holes, one of these being designated 122 in FIG. 4.

The first shaft unit 102c is snapped into engagement with the first control wheel unit 101a by means of a first snap connection 112 between the first shaft 102e and the first control wheel unit 101a. The first snap connection 112 includes two connection parts 112a of the first shaft unit 102c interlocking with two associated connection parts 112b (best seen in FIG. 7) of the first control wheel unit 101a. These associated connection parts 112a, 112b mutually engage. During the movement of the first shaft unit 102c, the connection parts 112a are pushed inwardly in the radial direction by the wheel sleeve 102g and, then, when the first shaft unit 102c is further moved and inserted, resiliently snap back to engage the associated connection part 112b. The connection parts 112b include a ramp or inclined surface 112c, which forces the pushable connection parts 112a in the radial direction during the movement of the first shaft unit 102c. Accordingly, the pushable connection parts 112a include a barb surface 112d which during the snap moves into engagement with an associated, opposed barb surface 112e of the connection parts 112b to secure the position of the first shaft unit 102c to the first control wheel unit 101a.

The second shaft unit 102d is snapped into engagement with the second control wheel unit 101b by means of a second snap connection 113 between the second shaft 102f and the second control wheel unit 101b. The second snap connection 103 includes two connection parts 113a in the form of resilient projections or pins of the second control wheel unit 101b which interlock with two associated connection parts 113b, embodied by recesses, of the second shaft unit 102d. These connection parts 113a, 113b are thus mutually engaging. The connection parts 113b includes a ramp or inclined surface 113c, which forces the pushable connection parts 113a inwardly in a radial direction during the movement of the second shaft unit 102d. Accordingly, the pushable connection parts 113a include a barb surface 113d which during the snap moves into engagement with an associated barb surface 113e of the other connection parts 113b to secure the position of the second shaft unit 102d to the second control wheel unit 101b.

A cap 105a is attached to a tip end 103b of the center shaft 103 by another snap connection 103c which is provided in a manner similar to the first and second snap connections 112, 113. Accordingly, the cap 105a includes two resilient and pushable connection parts 103d, whereas the tip end 103b includes associated two connection parts taking the form of recesses 103e. This snap engagement 103c is similarly be activated during or at the end of the insertion of the center shaft 103 into the control system 100.

The cap 105a covers and attaches a first multi-disc brake 110a of the first control wheel 101, see further below. The brake 110a is encased within a spacing defined by interior surfaces of the first wheel handle 101c. The cap 105a includes a brake knob 104a projecting in the assembly direction and upon rotation of which the brake 110a is activated to brake rotation of the first control wheel 101 and, thus, first shaft unit 102d.

A brake handle 104b for activation of a similar, second multi-disc brake 110b, which brakes the second control wheel 102 in a similar manner, is attached to the housing frame 116a.

Figure 3:
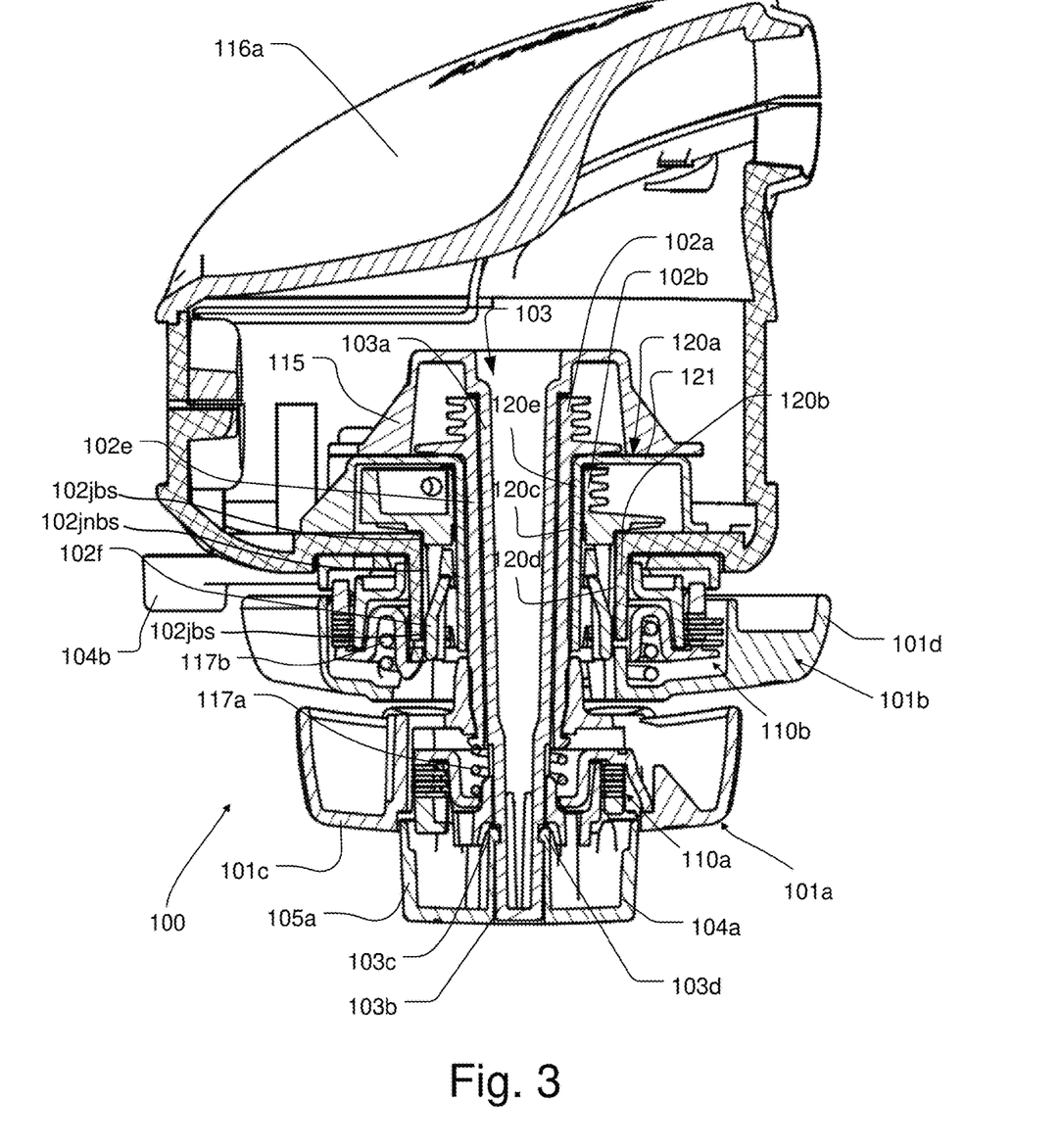
FIG. 3 shows a cross-sectional view taken along line III-III in FIG. 2.

As shown in FIG. 3, the first and second control wheels 101, 102 house the associated brakes 110a, 110b. Activation of each of the brakes 110a, 110b moves the brake from a released position to a braking position. A brake force of the brake 110a, 110b in the braking position brakes rotation of the associated control wheel 101, 102, respectively. The brake force is released in the released position. The brakes 110a, 110b each includes a stack of brake discs and a helical spring 117a, 117b, respectively.

The first and/or second wire drums 102a, 102b are pulleys. The first and second steering wires are attached to the wire drums 102a, 102b to be woundable on these, respectively.

The foregoing aspects are further embodied in the following exemplary items:

Item 1. An endoscope control system for performing a bending operation in a disposable insertion endoscope, the endoscope control system comprising:
an endoscope handle with a handle housing;
a first control wheel connected to a first wire drum for connection to a first steering wire of the endoscope, whereby rotation of the first control wheel relative to the handle housing about an axis of rotation controls the bending operation in a first dimension, the first control wheel comprising a bearing surface;
a second control wheel connected to a second wire drum for connection to a second steering wire of the endoscope, whereby rotation of the second control wheel relative to the handle housing about the axis of rotation controls the bending operation in a second dimension, the second control wheel comprising an outer bearing surface positioned farther from the axis of rotation than the bearing surface of the first control wheel; and
an outer bearing element forming part of or being rotationally fixed to the handle housing, the outer bearing element comprising an inner bearing surface positioned farther from the axis of rotation than the outer bearing surface of the second control wheel, the inner bearing surface of the outer bearing element abutting the outer bearing surface of the second control wheel so that rotation of the second control wheel is at least partly borne on the outer bearing element.

Item 2. The control system according to item 1, wherein the inner bearing surface of the outer bearing element and the outer bearing surface of the second control wheel each extends circumferentially about the axis of rotation.

Item 3. The control system according to item 1 or 2, wherein the inner bearing surface of the outer bearing element and the outer bearing surface of the second control wheel each includes at least two bearing surface parts, which are positioned at an axial distance from each other.

Item 4. The control system according to any one of the previous items, wherein the outer bearing element is in one piece with the handle housing.

Item 5. The control system according to item 4, wherein the outer bearing element is molded in one piece with the handle housing.

Item 6. The control system according to any one of the previous items, wherein the first control wheel comprises a first wheel handle and a first wheel sleeve, the first wheel sleeve connecting the first wheel handle to the first wire drum, the first wheel sleeve comprising the bearing surface of the first control wheel, wherein the second control wheel comprises a second wheel handle and a second wheel sleeve, the second wheel sleeve connecting the second wheel handle to the second wire drum, the second wheel sleeve comprising the outer bearing surface of the second control wheel, and wherein the second wheel sleeve encompasses at least part of the first wheel sleeve.

Item 7. The control system according to item 6, wherein the outer bearing element is an outer bearing sleeve that encompasses at least part of the second wheel sleeve.

Item 8. The control system according to any one of the previous items, further comprising an inner bearing element forming part of or being rotationally fixed to the handle housing, the inner bearing element comprising an inner bearing surface positioned farther from the axis of rotation than the outer bearing surface of the second control wheel, the inner bearing surface of the bearing element abutting the outer bearing surface of the control wheel so that rotation of the second control wheel is at least partly borne on the inner bearing element.

Item 9. The control system according to item 8, wherein the inner bearing element separates at least part of the first and second control wheels from each other so that rotation of the control wheels is mutually separated from each other.

Item 10. The control system according to item 8 or 9, wherein the inner bearing element is provided separately from and is fixed to the handle housing.

Item 11. The control system according to any one of the previous items, wherein the outer bearing element is an outer bearing sleeve that projects from a surface of the handle housing toward a wheel handle of the second control wheel.

Item 12. The control system according to any one of the previous items, wherein the second control wheel comprises a second wheel handle and a second wheel sleeve, the second wheel sleeve connecting the second wheel handle to the second wire drum, the second wheel sleeve comprising an inner part in one piece with the second wheel handle, the inner part of the second wheel sleeve being fixed to an outer part of the second wheel sleeve, the outer part of the second wheel sleeve being in one piece with the second wire drum, and wherein the outer bearing surface of the second control wheel is an outer surface of the outer part of the of the second wheel sleeve.

Item 13. The control system according to any one of the previous items, wherein the outer bearing element comprises a stop surface associated with a stop surface of the second control wheel so that when the second control wheel is rotated in a direction of rotation to an end position, mutual abutment of the stop surfaces prevents the second control wheel from rotating farther in that direction of rotation.

Item 14. The control system according to any one of the previous items, wherein the outer bearing element comprises an outer bearing sleeve having a wall with a wall thickness of more than one twentieth of a diameter or a cross-sectional extent of the outer bearing sleeve, and wherein the control system further comprises an inner bearing element forming part of or being rotationally fixed to the handle housing, the inner bearing element comprising an inner bearing sleeve having a wall with a wall thickness of less than one thirtieth of a diameter or a cross-sectional extent of the outer bearing sleeve.

Item 15. An endoscope comprising a control system according to any one of items 1 to 14.

Item 16. The endoscope according to item 15, further comprising the first and second steering wires and a distal tip or tip part that comprises a bending section connected to the first and second steering wires so that the control system can activate the bending operation of the bending section via the steering wires.

LIST OF REFERENCE SIGNS

1 Endoscope
2 Endoscope handle
3 Elongated insertion tube
3a Proximal end of insertion tube 3
3b Distal end of insertion tube 3
4 Tip
5 Bending section
6 Suction connector
7 Working channel port
100 Endoscope control system
101 First control wheel
101a First control wheel unit
101b Second control wheel unit
101c First wheel handle
101d Second wheel handle
102 Second control wheel
102a First wire drum
102b Second wire drum
102c First shaft unit
102d Second shaft unit
102e First shaft/sleeve
102f Second shaft/sleeve
102g First central part
102h Second central part
102i Outer bearing surface of first control wheel
102j Outer bearing surface of second control wheel
103 Center shaft
103a Shaft part
103c Snap connection
103d Connection parts
103e Recesses
104a Brake knob
104b Brake handle
105a Cap
110a First multi-disc brake
110b Second multi-disc brake
111 Stack of brake discs
112 First snap connection
112a Snap connection parts
112b Snap connection parts
112c Ramps
112d Barb surface
112e Barb surface
113 Second snap connection
113a Snap connection parts
113b Snap connection parts
113c Ramps
113d Barb surface
113e Barb surface
116 Handle housing
111 Stack of brake discs 116*a* Housing frame
116*b* Connection hole
117*a* Spring
117*b* Spring
120*a* Inner bearing element
120*b* Outer bearing element
120*c* Inner bearing surface of inner bearing element
120*d* Inner bearing surface of outer bearing element
120*e* Sleeve part
121 Inner bearing element frame
122 Screw hole
D Assembly direction

We claim:

1. An endoscope comprising:
an endoscope handle with a handle housing, the handle housing comprising two housing shells and an outer bearing element molded in one piece with one of the two housing shells; and
a control system including:
a first control wheel including a first shaft unit, a first control wheel unit and a first snap connection connecting the first shaft unit and the first control wheel unit, the first control wheel operable to rotate about an axis of rotation,
the first shaft unit comprising a first wire drum, a distal end, a first wheel sleeve having a bearing surface, and two connection parts at the distal end in the form of distally extending flexible fingers, each of the flexible fingers comprising a radially outwardly extending barb, and
the first control wheel unit comprising a first wheel handle and a first central part, the first central part comprising a cavity and two connection parts, each of the two connection parts of the first central part comprising a barb surface, the first snap connection formed when the distal end of the first shaft unit and the two connection parts of the first shaft unit are received in the cavity of the first central part with the radially outwardly extending barbs abutting the barb surfaces of the two connection parts of the first central part to prevent separation of the first control wheel unit from the first shaft unit;
a second control wheel including a second shaft unit, a second wheel handle and a second snap connection connecting the second shaft unit and the second wheel handle, the second shaft unit comprising a second wire drum and a second wheel sleeve having an outer bearing surface positioned farther from the axis of rotation than the bearing surface of the first control wheel; and
the outer bearing element comprising an inner bearing surface positioned farther from the axis of rotation than the outer bearing surface of the second control wheel, the inner bearing surface of the outer bearing element abutting the outer bearing surface of the second control wheel so that rotation of the second control wheel is at least partly borne on the outer bearing element,
wherein the outer bearing surface of the second control wheel includes two bearing surface portions axially spaced apart from each other and a non-bearing surface portion between the two bearing surface portions, and wherein the two bearing surface portions rotatably bear on the inner bearing surface of the outer bearing element.

2. The endoscope according to claim 1, wherein the inner bearing surface of the outer bearing element and the outer bearing surface of the second control wheel each extends circumferentially about the axis of rotation.

3. The endoscope according to claim 1, wherein the second wheel sleeve encompasses at least part of the first wheel sleeve.

4. The endoscope according to claim 3, wherein the outer bearing element comprises an outer bearing sleeve that encompasses at least part of the second wheel sleeve.

5. The endoscope according to claim 1, further comprising an inner bearing element forming part of or being rotationally fixed to the handle housing, the inner bearing element comprising an inner bearing surface positioned farther from the axis of rotation than the bearing surface of the first control wheel, the inner bearing surface of the inner bearing element abutting the bearing surface of the first control wheel so that rotation of the first control wheel is at least partly borne on the inner bearing element.

6. The endoscope according to claim 5, wherein the inner bearing element separates at least part of the first and second control wheels from each other so that rotation of the control wheels is mutually separated from each other.

7. The endoscope according to claim 5, wherein the inner bearing element is provided separately from and is fixed to the handle housing.

8. The endoscope according to claim 1, wherein the outer bearing element is an outer bearing sleeve that projects from a surface of the handle housing toward the second wheel handle.

9. The endoscope according to claim 1, wherein the second wheel sleeve includes an outer part opposite and in one piece with the second wire drum, the second wheel sleeve including the outer bearing surface between the outer part and the second wire drum, and the second control wheel comprising an inner part in one piece with the second wheel handle, the inner part being fixed to the outer part of the second wheel sleeve.

10. The endoscope according to claim 1, wherein the second control wheel comprises a stop surface, and wherein the outer bearing element comprises a stop surface associated with the stop surface of the second control wheel so that when the second control wheel is rotated in a direction of rotation to an end position defined by the stop surfaces, mutual abutment of the stop surfaces prevents the second control wheel from rotating farther in that direction of rotation.

11. The endoscope according to claim 1, further comprising an inner bearing element forming part of or being rotationally fixed to the handle housing, wherein the outer bearing element comprises an outer bearing sleeve having a wall with a wall thickness of more than one twentieth of a diameter or a cross-sectional extent of the outer bearing sleeve, and wherein the inner bearing element comprises an inner bearing sleeve having a wall with a wall thickness of less than one thirtieth of a diameter or a cross-sectional extent of the outer bearing sleeve.

12. The endoscope according to claim 1, further comprising a first steering wire and a second steering wire, and a distal tip or tip part that comprises a bending section connected to the first and second steering wires so that the control system can bend the bending section via the first and second steering wires.

13. The endoscope according to claim 12, wherein rotation of the first control wheel relative to the handle housing about the axis of rotation bends the bending section in a first dimension; and wherein rotation of the second control wheel relative to the handle housing about the axis of rotation bends the bending section in a second dimension.

14. The endoscope according to claim 5, further comprising a center shaft including a center shaft frame and a shaft part, wherein the inner bearing element includes an inner bearing element frame and a sleeve part having the inner bearing surface, wherein the center shaft frame is directly affixed to the inner bearing element frame, and wherein the shaft part extends through a connection hole in the handle housing and through the first wheel sleeve.

15. The endoscope according to claim 1, further comprising an inner bearing element forming part of or being rotationally fixed to the handle housing, the inner bearing element comprising an inner bearing sleeve having a wall with a wall thickness and an inner bearing surface abutting the bearing surface of the first control wheel so that rotation of the first control wheel is at least partly borne on the inner bearing element,
  wherein the inner bearing sleeve is positioned between the first wheel sleeve and the second wheel sleeve, the second wheel sleeve and the inner bearing sleeve being sized and configured so that the inner bearing sleeve does not bear the rotation of the second control wheel,
  wherein the outer bearing element comprises an outer bearing sleeve.

16. The endoscope according to claim 15, wherein the outer bearing sleeve comprises a wall including the inner bearing surface and having a wall thickness is less than one-tenth of an outer diameter of the outer bearing sleeve.

17. The endoscope according to claim 16, wherein the wall thickness of the inner bearing sleeve is less than the wall thickness of the outer bearing sleeve.

18. The endoscope according to claim 15, wherein the inner bearing sleeve consists essentially of a polycarbonate polymer.

19. The endoscope according to claim 15, wherein the inner bearing element comprises an inner bearing element frame connected to the inner bearing sleeve and the handle housing, the inner bearing element surrounding the second wire drum.

20. The endoscope according to claim 1, further comprising a center shaft forming part of or being rotationally fixed to the handle housing, the first wheel sleeve receiving the center shaft with the bearing surface facing and abutting an outer bearing surface of the center shaft so that rotation of the first control wheel is at least partly borne on the center shaft,
  wherein the outer bearing element is molded in one piece with the handle housing and comprises an outer bearing sleeve having a wall including the inner bearing surface, and
  wherein the second wheel sleeve is positioned between the first wheel sleeve and the outer bearing sleeve.

* * * * *